United States Patent [19]

Hawkins et al.

[11] Patent Number: 4,776,879

[45] Date of Patent: Oct. 11, 1988

[54] WATER INSOLUBLE TRIAZONE FERTILIZER AND METHODS OF MAKING AND USE

[75] Inventors: Edwin F. Hawkins, Baton Rouge, La.; John G. Clapp, Jr., Greensboro, N.C.

[73] Assignee: Triazone Corporation, Parsippany, N.J.

[21] Appl. No.: 46,647

[22] Filed: May 7, 1987

[51] Int. Cl.$^4$ .................... A01N 43/64; C07D 251/08
[52] U.S. Cl. .......................................... 71/93; 544/220
[58] Field of Search ............................ 544/220; 71/93

[56] References Cited

U.S. PATENT DOCUMENTS 4,554,005 11/1985 Hawkins .................................. 71/30
4,599,102  7/1986 Hawkins .................................. 71/30

Primary Examiner—Richard A. Schwartz
Attorney, Agent, or Firm—William T. Hough

[57] ABSTRACT

In a preferred embodiment, a high-yield method producing novel water insoluble triazone compositions with a typical analysis, prior to separation of the insoluble triazone crystals, has components in amounts as follow, percentages being based on the total weight of the reaction product; unreacted urea at about 10%, total percentage of nitrogen from urea at about 4.7, with maximum total nitrogen at about 30 percent, with the yield of triazone at about 75 percent, produced by a novel method in which urea or substituted urea and pH adjusted to and maintained at about pH 9.0 by addition preferably of potassium hydroxide 45% aqueous solution, while mixing thoroughly and heating for about one hour at a temperature of about 85 degrees Centigrade, however keeping below the boiling point of the aldehyde, utilizing water or other solvent such as alcohol or other equivalent to maintain fluid conditions. The amine is thereafter slowly added while the maintaining temperature below about 65 degrees during the amine addition, and while continuing to maintain the pH at about 9.0. Thereafter, the mixture is heated to and maintained at about 85 degrees Centigrade for about one hour, and thereafter cooled to about 30 degrees Centigrade, followed by filtering-off triazone crystals, washing the precipitate crystals with reagent alcohol or water, and drying the crystals. In the above procedure, the molar ratio of various ingredients are typically as follow: urea/aldehyde/ammonia (or amine) at about 0.5/1/0.5, except that for ethylene diamine or other diamine, the ratio is at about 0.5/1.0/0.25. A number of water-insoluble triazones produced by this method have been found to be beneficial fertilizers. Novel water-insoluble triazone compositions include typically, 5-B-ethanol triazone, 5-methyl triazone, 5, 5' ethylene ditriazone, thiotriazone, 5-methyl thiotriazone, 5-B-ethanol thiotriazone, 4,6-dimethyl-5-B-hydroxyethyl thiotriazone. These novel triazones are applied by any conventional or desired method to land or crops as fertilizer alone or in combination with other fertilizers.

51 Claims, No Drawings

WATER INSOLUBLE TRIAZONE FERTILIZER AND METHODS OF MAKING AND USE

This invention is directed to a novel method for producing water-insoluble triazones, some of which are novel, and to the novel use of various water-insoluble triazones as ferilizer.

BACKGROUND OF THE INVENTION

Prior to this invention, the present joint inventor Hawkins was granted U.S. Pat. Nos. 4,554,005 granted Nov. 19, 1985 and 4,599,102 granted July 8, 1986 respectively, directed to water-soluble triazone compositions and their methods of preparation and use as foliar fertilizers, and is obtaining further patent coverage on improved method for their making, together with other novel water-soluble triazones. It is assumed for the purposes of this patent application that a material is considered to be water-soluble if a solution containing at least eight percent or more by weight of nitrogen can be prepared at standard temperature and pressure, and likewise is considered to be water-insoluble if less than eight percent water soluble nitrogen solution can be prepared from the substances.

While the inventions of those patents represented major advances in the art, it was desirable to obtain novel water-insoluble triazone(s), of which is was not at all clear whether or not many such insoluble triazone compounds could or could not be produced or if so, in any significant and practical yield, as well as many never having exited before. With regard to the water-insoluble triazones, just as with the water-soluble triazones, it is not possible to predict whether or not a particular triazone will have beneficial fertilizer utility and/or whether or not any particular one or more will possibly adversely affect or kill vegetation, as opposite to helping it. Thus far, that normally can be ascertained solely by field trial and error, toxicity to plant life not being predictable. Thus, no advance utility as a fertilizer for either water-soluble or water-insoluble triazones, is predictable prior to the present invention.

It has also been desirable to substantially increase the yield of the water insoluble triazone compositions to a significant degree such that they may be economically and practically produced on a commercial scale, by novel method(s) of this invention, since prior methods of production of water-insoluble triazones heretofore has been considered undesirable due to impractical low yield, as well as due to undesirable other aspects of prior methods.

OBJECTS OF THE INVENTION

Accordingly, objects of the present invention include the obtaining of nove water-insoluble compositions and a novel method obtaining unexpectedly high yields of water-insoluble triazones(s) in the reaction product as compared to what was known or possible heretofore, and new use of particular water-insoluble triazones, including some novel water-insoluble compounds, as fertilizers.

Another object is to ascertain whether there exist particular ranges to various ingredients, within such ranges unexpectedly improved yields are obtainable of water-insoluble triazones utilizable as fertilizers.

Another object is to ascertain whether among apparent equivalents for reactants, there exist particular ones that obtain unexpectedly improved yields of water-soluble triazones, and if so, the particular ranges in which such improved yields may be achieved for water-insoluble triazones.

Another object is to ascertain and produce novel water insoluble triazones having utility as fertilizer, particularly as nitrogen fertilizer, which novel triazones are not significantly nor fatally toxic to plants when applied as water-insoluble fertilizer, especially as applied to or into the soil.

Another object is to ascertain variations in the method of production of water-insoluble triazones which significantly increase or alternatively decrease high yields of water soluble trizones.

Other objects become apparent from the preceding and following disclosure.

One and more objects are obtained by the invention as described herein.

SUMMARY OF THE INVENTION

Broadly, the invention may be described as a novel method obtaining unexpectedly high yield of water-insoluble triazone compositions of the above-noted patents and of producing novel water-insoluble triazone compositions noted below, and novel use of particular water-insoluble triazone compositions as fertilizers.

More particularly the inventive method, in a preferred embodiment, novely utilizes a critical caustic to adjust or maintaining particular pH during initial reaction, as well as having ascertained novel ranges and ratios and operating temperature ranges and periods of reaction, each of which contribute to the obtaining of unexpectedly high and improved yield(s) of the water-insoluble triazone(s) of this inventive process. After cooking is completed, the reaction media is cooled to about 35 degrees Centrigrade or less, with a resulting maximum formation of crystals of the water-insoluble triazone, after which the crystals are separated by filtration or by centrifuging and normally washed with alcohol. Thereafter the crystals are dried and packaged.

This method of producing water-insoluble triazone compositions includes, within aqueous or other diluting or solvent media, the initial cooking (reacting) of a urea-like component—such as urea or substituted urea, with an aldehyde—such as formaldehyde, and an ammonia-source reactant—such as ammonia and/or an amine, diamine, or triamine (including substituted amines) while maintaining pH within a preferred range by intermittent or continually adding preferably potassium hydroxide within a preferred range. The amount of potassium hydroxide preferably required to be added, broadly ranges between about 0.5 percent and 5.6 percent by weight of total reactants, more preferred results being expected by a narrow range within from about 0.5 percent to about 1.0 by weight.

In addition to the above-noted criticality of the pH, a preferred higher yield can be expected if pH is maintained within a preferred range, preferred higher yields may be expected if other variables are maintained within narrow preferred ranges as follow. In the initial reactants, the urea-like compound(s) relative to the aldehyde-like compound(s) preferably has a molar weight ratio critically ranging broadly from about 0.45 to about 0.55, more preferably from about 0.49 to about 0.51. Ammonia or ammonia-source(s) relative to aldehyde-like compound(s), preferably has a molar ratio of broadly critically from about 0.3 to about 0.50, more preferably from about 45 to about 0.50. The most preferred results has been obtained from ratios of about 0.5/1/0.5 of urea/aldehyde/ammonia and/or amine. It is to be understood that in the statement of these ratios for urea and aldehyde and ammonia and/or amine, the approximate same ratios apply to the equivalents substituted for one or more of these reactants, such equivalents being discussed herein below. For both the initial and the second phases of heating, the temperature of reactants is within the broad range preferably of about 87 degrees Centigrade to about 92 degrees Centigrade, preferably critically within the range of about 90.5 degrees Centigrade to about 91.5 degrees Centigrade. The initial cooking is for a period preferably broadly from about 15 minutes to about 55 minutes, more preferably from about 40 minutes to about 50 minutes. The second stage ranges critically from about 7 minutes additional cooking time up to about 35 minutes, preferably 10 minutes to about 20 minutes. Total cooking time, as the sum of times of the initial and second stages of cooking, preferably should not exceed about 70 minutes, more preferably about 60 minutes. During the initial phase or stage of cooking, the pH is maintained preferably within the range of about 8.6 to about 9.3, more preferably critically from about 8.7 to about 9.1. Nitrogen source reactants are typically employed in amounts such that total nitrogen in the resulting triazone composition ranges from preferably about 22.5 to about 32 percent, based on total weight of all reactants as previously set-forth above, and normally from about 26 to about 30 percent.

During the initial stage, the caustic added to maintain pH is preferably KOH aqueous solution ranging from aqueous solution of about 35 to 55 percent, preferably aqueous solution of from about 40 to 50 percent, optimally an aqueous solution of about 45 percent. As a standard, a dilution normally commercially available, the above-noted amount (ranges) stated for the potassium hydroxide utilized in the method of the present invention, has been the conventional 45 percent aqueous solution; accordingly, if other aqueous dilutions-percentages of potassium hydroxide are alternatively employed, the above-specified preferred employable-amounts (ranges) of aqueous potassium hydroxide would be interpolated to different equivalent ranges, not altering the nature of the invention. It has been experimentally ascertained that other aqueous caustics such as typically sodium hydroxide aqueous solution (NaOH aqueous solution) may be employed (the sodium hydroxide ranging from an aqueous solution of about 40 to 60 percent) to obtain lesser yields. Unexpectedly improved higher yields of water-insoluble triazone may be expected by the preferred use of the potassium hydroxide within the preferred range specified above. Other caustics which likewise would obtain unexpected inferior yield typically would be expected to include other normally recognized equivalents such as lithium hydroxide and/or sodium hydroxide, or other strong cuastic or mixtures thereof. Sodium hydroxide would have been expected to be the most likely equivalent as a substitute for potassium hydroxide, but such does not appear to be the case on the basis of yield, it appearing that preferred supperior yields are obtained within specified ranges of the neutralizing aqueous potassium hydroxide.

Improved yield of insoluble triazone may be expected by commencing addition of the caustic (for the initial stage of reaction) at substantially the end of the adding of ammonia or ammonia-type compound to the remaining others of the initial reactants. The caustic is preferably added at thereafter at any one or more point(s) in time as might be required in an amount sufficient to maintain the above-stated pH.

In the preceding novel method, the ingredient-reactants and equivalents thereof are as follow. Urea-source reactants may be urea and/or substituted urea. The ammonia-source may be preferably anhydrous ammonia or aqua ammonia and/or a primary amine. The aldehyde source may be formaldehyde, acetaldehyde or substituted aldehydes or the like.

In an alternate preferred second method, the urea-source and the aldehyde are mixed together in a water solution while keeping the temperature below the boiling point of the aldehyde, and thereafter the ammonia or amine-source is added sufficiently slowly as to have the temperature rise to not more than about 90 degrees Centigrade, after which miving is continued for an additional mix time of about 30 minutes or more at about 90 degrees Centigrade while controlling pH at about pH 9.0, followed by cooling to about 30 degrees sufficiently to maximize crystal formation, followed by separating the crystals by filtration and typically thereafter washing the crystals as above-noted. The pH is maintained between about pH 8.6 and 9.3, preferably about pH 8.9–9.1.

In this latter embodiment, the proportions of reactants are used in the same broad and narrow ratios noted for the other preceding method of making, and the reaction additional-mixing temperature typically normally ranges from about 85 to about 93, preferably from about 88 to 92 degrees Centigrade. The period of additional mix ranges typically from about 20 to 40 minutes, preferably from about 25 to 35 minutes. In contrast to the above-noted emperical-formula ratio of urea/aldehyde/ammonia discussed-above, it has been found that improved yield can be expected by employing the urea-source in a small excess relative to aldehyde, on a molar weight ratio basis.

In another novel third method involving specifically solely the production of thio-triozones, the method correspond to that of the above-noted second method, except that prior to addition of the ammonia or amine source, thiourea (or thiourea-source) is mixed with the aldehyde source in a suitable solvent (water or other non-reactive solvent or diluent), and pH is adjusted to and maintained at between about 8.7 to about 9.3, preferably between about 8.9 to 9.1, thereafter heating the mixture to a temperature between about 35, preferably 40 degrees and 55, preferably 50 degrees Centigrade while preferably continuing to stir or mix for an additional period of from about ¾ hr. up to about three hours, preferably from about 1 to 2 hours. Thereafter the ammonia or amine are added, preferably sufficiently slowly that temperature is maintained at not more than the above-noted maximum of 55 degrees Centigrade. Thereafter mixing continues for an additional mixing period of from about 0.75–2 hours, preferably about 1 to 1.5 hours, within the above-noted temperatures, followed by cooling as noted for the preceding second method, filtering, and washing and drying and packaging, as above-noted. For thiourea, there may be substituted-thiourea such as dimethyl thioureas and the like. Likewise, the same as for other methods typical aldehydes are formaldehyde, acetaldehyde, propionaldehyde and the like. Any primary or substituted amine may be substituted for ammonia, such as methyl amine, monoethanol amine, diethyl amine, amino methyl propanol, 1,3-diamino-2-hydroxy propane, and the like.

Particular novel water-insoluble triazones produced by the preceding methods include the following:

(A) thiotriazone:

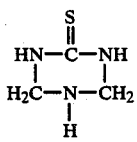

produced from thiourea, formaldehyde and ammonia; and (B) 5-methyl thiotriazone:

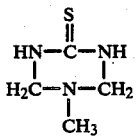

produced from thiourea, formaldehyde and methylamine.

(C) 5-B-ethanol thiotriazone:

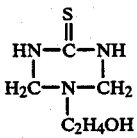

produced from thiourea, formaldehyde, and monoethanolamine; and (D) 4,6 dimethyl-5-B-hydroxyethyl thiotriazone:

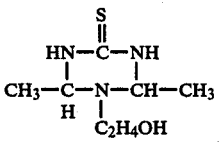

produced from thiourea, acetaldehyde, and monoethanolamine.

Other thiotriazones within the scope of the present invention, producable by the preceding novel methods, typically include:

(E) 1-3 dimethyl thiotriazone, produceable from 1,3 dimethyl thiourea, ammonia and formaldehyde; and (F) 1-3 dimethyl-5-Beta ethanol thiotriazone; and (G) 4-6 dimethyl thiotriazone; and (H) 1,3,4,6 tetramethyl thiotriazone; and (I) 1,3,4,5,6 pentamethyl thiotriazone; and (J) 5,5' ethylene dithiotriazone of the structural formula:

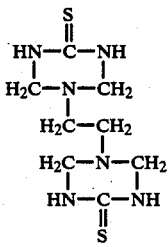

and (K) 1-3-5-trimethyl thiotriazone; and 4,6,5 trimethyl thiotriazone; and (L) 4-6 diethyl thiotriazone; and (M) 4-6 diethyl-5-B hydroxyethyl thiotriazone; and Other triazones produceable by the novel methods of the invention typically include:

(N) Ethyl thiotriazone; and (O) S-adamantane triazone ($C_{13}H_{21}N_3O$) having a molecular weight of 235 (17.9%N); produced from urea, formaldehyde and adamantanamine; and (P) 5-(5,6-dimethyl-1,2,-4-triazine)triazone ($C_8H_{12}N_6O$) having a molecular weight of 208 (40%N); produced from urea, formaldehyde and 3-amino-5,6-dimethyl-1,2,4 triazine; and (Q) 5-(1,3 dimethyl uracil) triazone ($C_9H_{15}N_5O_3$) having a molecular weight of 239 (29.3%n); produced from urea, formaldehyde and 6-amino-1,3-dimethyl uracil; and (R) 5(furfuryl) triazone ($C_8H_{11}N_3O_2$) having a molecular weight of 181 (23.2%N); produced from urea, formaldehyde and furfurylamine; and (S) 5-hydantoinamid, triazone ($C_8H_9N_7O$) having a molecular weight of 242 (34.7%N); produced from urea, formaldehyde and allantoion;

(T) 5 purine triazone ($C_8H_{17}N_7O$) having a molecular weight of 219 (44.7%N); produced from urea, formaldehyde and adenine-6 amino purine (growth regulator); and (U) 4,6-propyl-5-betahydroxyethyl triazone ($C_{11}H_{24}N_3O_2$) having a molecular weight of 230 (18.3%N); produced from urea, isobutyraldehyde and B-ethanol-amine.

(V) Ethyl triazone produced from urea (or equivalent), ammonia and formaldehyde (or other aldehyde equivalent).

(W) isopropyl ditriazone of the structural formula

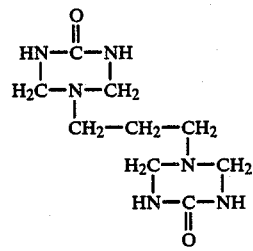

(X) methyl triazone produced from urea (or equivalent), methyl amine, and formaldehyde (or equivalent).

(Y) 5,5'-ethylene ditriazone.

(Z) 5-B, hydroxyethyltriazone.

(AA) 1,3 ditriazone, 2-hydroxypropane (BB) tris (ethyl triazone) amine.

(CC) 1, triazone, 3, (2,5 dioxo-4-imidazolininyl) urea.

(DD) 5-ethyl thiotriazone.

As experimentation and research developed further, it was unexpectedly discoved that there existed an additional fourth and fifth methods described hereinbelow, by which much superior results could be achieved, apart from being different method as contrasted to the foregoing. By the following fourth and fifth described methods, the yields are improved of the insoluble triazone and/or thiotriazone, and/or there are fewer by-products—i.e. more complete conversion and/or a purer insoluble product, and the mother-liquid remaining after separation of the insoluble crystals, contains fewer by-products of other formed soluble compounds and of initial reactant(s).

More particularly, the fourth method, while utilizable to produce either insoluble triazones (or substituted triazones) or insoluble thiotriazones (or substituted thiotriazones), superior results of the above-described nature, are obtained by the fourth method in the production of non-thiotriazones. In contrast, the fifth method described below, has been likewise found to obtain superior results in the production of the thiotriazones.

The fourth method is as follows.

The initial reactants employed include (and are normally and preferably limited to) a urea-type compound-source such as typically urea and/or a mixture of urea and formaldehyde, an aldehyde-type compound-source such a formaldehyde, and a diluent, such a water and/or another diluent for dissolving and/or suspending the reactants, using the diluent in a diluting amount sufficient for the foregoing reactant to form and exist as a reaction mixture. The preceding reactants are thereupon mixed, forming the reaction mixture (and/or solution). To the mixed reaction mixture, there is added a caustic in an amount sufficient to adjust pH to a pH within a pH range of from about pH 8.6 to about pH 9.3, and sufficiently to thereby form a pH-adjusted reaction mixture. Thereafter, to the pH-adjusted reaction mixture, there is added an ammonia-type compound-source such as ammonia and/or an amine and/or substituted amine; it/they is/are added in an amount sufficient to form an ammonia or amine-type reaction product. When the ammonia-type compound-source includes an amine (or substituted amine), the rate of addition of the ammonia-type compound-source is added at a sufficiently slow rate of addition, relative to the surrounding natural or implemented cooling-conditions, as to maintain temperature up to a temperature below a boiling point of the amide (or substituted amine), relative to rate of cooling of the ammonia and/or amine-type reaction product. Thereafter, the resulting ammonia, amine or substituted-amine-type reaction product is heated to a temperature within a temperature range of from about 85 degrees Centigrade to about 93 degrees Centigrade for an initial heating period ranging from about 15 minutes up to about 30 minutes and/or sufficiently to form a final reaction product mixture while again (a second time) adding caustic in an additional amount sufficiently to maintain pH within the above-described pH range (described for the initial heating period). Thereafter, further addition of caustic is terminated, while thereafter continuing heating the final reaction product mixture within the temperature range above-described for the initial heating, for an additional heating period ranging from about 5 minutes to about 25 minutes, sufficiently to form a cooked product mixture. Thereafter, the cooked product mixture is cooled sufficiently such that insoluble triazone becomes substantially crystallized triazone apart from remaining liquid product and substances dissolved therein. Thereafter, the crystallized triazone is separated from the remaining mother liquor and products dissolved therein, by any of desired and/or conventional routes/methods that are not detrimental to the crystallized triazone. Typically, centrifucation and/or filtration may be employed, for example.

In this fourth method, preferably the diluent includes a major proportion of water, possibly solely water.

In a preferred embodiment of this fourth method, the temperatures of reaction as described-above for this fourth method, are maintained within a temperature range of from about 89 to about 91 degrees Centigrade.

In this fourth method, preferably upon the first-adding and the second adding of caustic, the caustic is added in amounts such that the pH-alkalinities range between about pH 8.9 and pH 9.1.

In a preferred embodiment of the fourth method, initial heating ranges from about 15 to about 25 minutes, and the additional subsequent heating ranges from about 7 minutes to about 15 minutes.

In this fourth method, preferably the cooling includes cooling-down the cooked-product mixture to at-least below about 30 degrees Centigrade.

In the fourth method, preferably the urea-type compound is at-least predominantly urea, and the aldehyde-type compound-source includes at-least predominantly formaldehyde, and the caustic is at-least predominantly potassium hydroxide.

In this fourth method, preferably after the separating of the insoluble crystals, there is included drying the separated crystals of insoluble triazone at a temperature of from about 60 degrees to about 75 degrees Centigrade for at-least about 36 hours.

Also in the foregoing fourth method, preferably in the cooling, prior to the separating, that cooling includes the cooling of the cooked product for a final cooling period of at-least about 60 hours at a temperature of between about 0.5 degrees and about 2 degrees Centigrade.

Additionally, in the fourth method, preferaly after the separating of the crystals, they are dried at a temperature of from about 65 degrees to about 72 degrees Centigrade for at-least about 44 hours.

The fifth above-noted method, utilized most favorably in the production of various thiotriazones as previously mentioned, is as follows.

The initial reactants include (and are normally and preferably limited to) urea-type compound-source such as urea and/or substituted urea and/or mixture(s) thereof with aldehyde (or substituted aldehyde), and an aldehyde-type compound-source such as formaldehyde and/or acetaldehyde and/or substituted forms thereof, and/or the like, and a diluent such as water and/or other diluent(s) in an amount sufficient to form a reaction mixture (and/or solution) of reactants. These initial reactants are thereupon admixed sufficiently to form a reaction mixture (such term intended to include mixture and/or solution). To the reaction mixture, there is thereafter added ammonia and/or an ammonia-providing type compound and/or amine-type and/or substituted-amine-type compound, in amount(s) sufficiently to form an ammonia or amine-type product. When the ammonia-type compound is or includes an amine and/or substituted amine, rate of addition of the ammonia-type compound is a rate sufficiently slow during the addition, as to maintain temperature up to a temperature below a boiling point of the amine(s) and/or substituted-amines, relative to normal cooling conditions and/or initiated cooling conditions to which the mixture is subjected, relative to rate of cooling of the ammonia and/or amine(s) and/or substituted-amines being added. Thereafter, the thereby-formed ammonia and/or amine and/or substituted-amine-type product(s) are cooled sufficiently that insoluble triazone(s) become substantial crystalized as crystallized triazone(s) apart from remaining mother liquor product and substance(s) dissolved therein. Thereafter, the insoluble crystalized triazone(s) is/are separated from remaining liquid product and substances dissolved therein.

In the foregoing fifth method, preferably the initial mixing is continued for a period of at-least about 15 minutes.

In the fifth method, preferably the diluent includes a major proportion of water.

In the fifth method, preferably the aldehyde-type compound includes at-least predominantly formaldehyde.

In the fifth method, preferably the cooling, prior to the separating, includes cooling the ammonia and/or amine-type and/or substituted-amine-type product for a final cooling-period of at-least 48 hours at a temperature between about 0.2 degrees and about 6 degrees Centigrade.

In the fifth method, preferably after separating, the crystallized triazones are dried at a temperature of from about 60 degrees to about 75 degrees Centigrade for at-least about 36 hours.

In this fifth method, also preferably, during the cooling prior to separating of the insoluble crystals of triazone, the cooked product is cooled for a final cooling period of at-least about 60 hours at a temperature of between about 0.5 degrees and about 2 degrees Centigrade.

Preferably, after separating the insoluble crystals of triazone from the mother liquid, the crystals are dried at a temperature of from about 60 degrees to about 75 degrees Centigrade for at-least 36 hours.

Also, preferably in the fifth method, prior to separating the insoluble crystals from the mother liquid, the cooked product is cooled for a final cooling period of at-least 60 hours at a temperature of between about 0.5 degrees and about 2 degrees Centigrade.

After separating the insoluble crystals, preferably they are dried at a temperature of from about 65 degrees to about 72 degrees Centrigrade for at-least about 44 hours.

In any and all embodiment of the various methods described above, where the term "preferred" is used, it is intended to mean that for unexpectedly superior and critical results in the nature as previously described, that (those) particular embodiment(s) are in fact critical, based on actual experimentation, observation and study of the methods and products formed thereby.

Additional novel products, in addition to those previously noted, include the following:
(a) 5-B, hydroxyethyltriazone.
(b) 5, 5'-ethylene ditriazone.
(c) 1,3 ditriazone, 2 hydroxypropane.
(d) tris (ethyl triazone) amine.
(e) 1, triazone, 3, (2, 5 dioxo-4-imidazolininyl) urea.
(f) methyl thiotriazone.
(g) ethyl thiotriazone.
(h) ethanol thiotriazone.
(i) 5-ethyl thiotriazone.
For all of the reactions of the various methods, unless otherwise specified, the molar ratios are as follow:

For monoamines such as methyl amine, ethyl amine, ethanol amine, and the like:
urea/HCHO/amine at 1/2/1;
for diamines such as ethylene diamine:
urea/HCHO/amine at 2/4/1

For triamine such as tris (2-amino ethyl) amine:
urea/HCHO/amine at 3/6/1
i.e. for complete reaction, one mole of urea (for example) and two moles of formaldehyde (for example) are needed for each primary amine group in the amine molecule.

A small excess of urea and formaldehyde may be desirable to insure that all of the amine is reacted.

In all of the above formulations, typical substitutions may be made as follow: for urea, there may be substituted in whole or in-part thiourea, dimethyl urea, ethyl urea and the like. For formaldehyde, there may be substituted in whole or in-part, acetaldehyde, propionaldehyde, and the like.

It is to be noted that even when a novel insoluble-triazone produced by the method(s) of this invention such as above-noted compounds, in some instances lack utility as a fertilizer because of phytotoxicity or other detriment to plant life, that particular triazone nevertheless has a utility as a weed killer or defoliant or growth regulator or the like, i.e. a different or opposite utility.

Some of the above-noted preceding listed compounds are limited to water-insoluble compounds of the generic formulas described as follow, but must necessarily at this point in time be identified in association with the method of this invention, noting that these compounds may be produced also in lesser yields by the method of the above-noted prior patents of the inventor, but also recognizing that until actual extensive experimentation, it was not possible to ascertain that these compounds could be produced nor that if produced that they would be insoluble and stable as to shelf life and at varying storage temperatures and periods of time.

As a further practice of increasing the yields of the solid products, the mother liquior from one crystallization may be utilized as the diluent to product subsequent batches of the same water insoluble triazone.

Secondly, the mother liquor itself contains nitrogen from the small amount of unreated urea and from the dissolved (soluble) triazones therein, and with adjustment may be used as a nitrogen source for fertilizer thus substantially eliminating any problem of dispoosal of waste products.

A typical analysis of mother liquor is as follows, however recognizing that upon each recycling of the mother liquor, the concentrations increase as well yields of insoluble triazone resulting from the recycled mother liquor.

| MOTHER LIQUOR ANALYSIS | | |
|---|---|---|
| Insol. Triazone produced: | Methyl Triazone | Hydroxyethyl triazone |
| Total % N | 15 | 20 |
| % urea | 3.9 | 3.0 |
| % methyl triazone | 14.3 | — |
| % B—hydroxy ethyl triazone | — | 22.5 |
| % unsubstituted triazone | — | 1.1 |

Novel insoluble thiotriazones generically include at least the following:

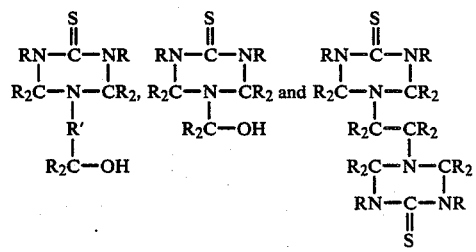

where R is hydrogen, alkyl (such as methyl, ethyl, dimethyl, trimethyl, etc.), and/or alkyl-substituted alkyl, and where R' is alkyl-substituted alkylene, or alkylene; and

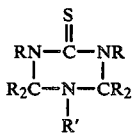

where R is hydrogen, alkyl (such as methyl, ethyl, dimethyl, trimethyl, etc.), alkyl-substituted alkyl, alkylamine and/or cycloalkyl, and where R' is hydrogen, alkyl or alkyl-substituted alkyl, cycloalkyl or alkylamine.

The typical approximate analysis of various products prepared by the preceding preferred methods are shown as follow in Table I, in terms of percentage yields based on amine addition, for crude product (not crystallized).

TABLE I

| Component | Yield | W/D* % C | W/D % H | W/D % N | W/D % O | W/D % S |
|---|---|---|---|---|---|---|
| Ethylene | 47% | 38.4/ | 7.2/ | 34.6/ | 19.8/ | — |
| ditriazone | | 42.1 | 7.0 | 36.9 | 14.0 | — |
| Methyl | 76% | ND**/ | ND/ | 32.2/ | —/ | —/ |
| thiotriazone | | 36.6 | 6.9 | 32.1 | — | 24.4 |
| Hydroxyethyl | 40% | ND/ | ND/ | 25.9/ | ND/ | 20.9/ |
| thiotriazone | | 37.3 | 6.8 | 26.1 | 9.9 | 19.9 |
| Methyl | 60% | 40.8/ | 7.8/ | 36.2/ | 15.2/ | —/ |
| triazone | | 41.8 | 7.8 | 36.5 | 13.9 | — |
| Hydroxy | 35% | ND/ | ND/ | 28.8/ | —/ | —/ |
| ethyl triazone | | 41.4 | 7.6 | 29.0 | 22.0 | — |
| Thio triazone | 42% | 32.9/ | 7.0/ | 38.8/ | —/ | 22.6/ |
| | | 30.8 | 6.0 | 35.9 | — | 27.3 |

NOTE
*Wet/Dry = W/D
**Not determined = ND

Triazone solubilities for various water-insoluble triazones are typically as follow, as measured at 20 degrees Centigrade in water:

| | Wt. % Soluble | % N | % S |
|---|---|---|---|
| Methyl triazone | 13.1% | 4.8 | — |
| Hydroxy ethyl triazone | 21.4 | 6.2 | — |
| Thio triazone | 15.6 | 5.6 | 4.3 |
| Hydroxy ethyl thio triazone | 29.9 | 7.8 | 5.9 |

As a typical illustration that not all random methods may be utilized to produce the insoluble triazones of this invention, the following Example I is an actual experiment that did not work, i.e. was an unsuccessful procedure.

EXAMPLE I

| Reactants-formulation: | Wt. % | grams |
|---|---|---|
| (A) Thiourea | 31.1 | 1244 |
| (B) Paraformaldehyde | 24.5 | 1380 |
| (C) Anhydrous ammonia | 7.0 | 280 |
| (D) Water | 37.4 | 1496 |

Procedure:
(I) Mixed together, A, B and C-above and adjust pH to 8.5 with 45% sodium hydroxide.

(II) Slowly added D while cooking at 64 degrees Centigrade at pH 7.2.

(III) Cooked for 45 minutes at 90 degrees Centigrade with pH at 9.0 (plus or minus 0.3).

(IV) Cooked for an additional 10 minutes at 90 degrees Centigrade (plus or minus 1 degree Centigrade) without pH control.

(V) Cooled to 70 degrees Centigrade and filter while hot.

Results:

A gummy white insoluble precipitate formed. It was very difficult to filter or clean-up. Upon storing in the refrigerator overnight at 35 degrees Centigrade, no further precipitate, except the water insoluble gum. The gum product had no apparent utility.

With similar unsatifactory results, several other procedures likewise proved to be unsatisfactory.

In evaluation of typical insoluble triazones of this invention, methyl triazone and hydroxyethyl triazone were evaluated and results summarized as potential nitrogen fertilizer sources, as follows.

EXAMPLE II

The first field experiment to evaluate a solid triazone product was conducted on a sod farm near La Belle. Fla., on "Floratana" St. Augustine and "419" Hybrid Bermuda.

Since phytotoxicity of leaf burn is a major consideration for conventional liquid applied nitrogen products to turf grasses, this test was designed to evaluate the solid (methyl triazone) in comparison to liquid urea and UAN (urea-ammonium nitrate solution). Liquids were applied at spray rates of 4.0 gal./1000 sq. ft.. Three nitrogen rates, 1.5, 3.0 and 6.0 lbs. N/1000 sq. feet, were used to insure that phytotoxicity would occur. Color response ratings were also measured.

Results are noted in the following Table II. On St. Augustine, no injury was noted for methyl triazone at rates of 1.5 and 3.0 lbs. N/1000 sq. ft.; whereas significant injury occurred for the other nitrogen sources. Less injury also occurred for bermuda.

Unexpectedly, a significant and good color response developed following the methyl triazone application. Since the urea and UAN () was applied with water as a spray, it was anticipated that a more rapid color response would follow. This was not the case, as noted in Table II.

TABLE II

| N Source (Note "a") | Rate Lbs. N/ 1000 sq. ft. | Phytotoxicity (N. b) | | Color (N. c) | |
|---|---|---|---|---|---|
| | | St. Aug. | Berm. | St. Aug. | Berm. |
| Methyl triazone | 1.5 | 0.00 | 1.00 | 2.67 | 3.00 |
| Urea | 1.5 | 1.83 | 1.83 | 2.00 | 0.50 |
| UAN | 1.5 | 2.17 | 2.17 | 2.00 | 0.83 |
| Methyl triazone | 3.0 | 0.00 | 1.33 | 2.50 | 4.67 |
| Urea | 3.0 | 3.17 | 2.50 | 2.00 | 0.00 |
| UAN | 3.0 | 3.50 | 3.33 | 2.00 | 2.67 |
| Methyl triazone | 6.0 | 0.17 | — | 4.25 | — |
| Urea | 6.0 | 3.33 | — | 2.50 | — |
| UAN | 6.0 | 4.17 | — | 1.5 | — |

Notes:
a Treatments applied to St. Augustine on 5-15-85 and to Bermuda on 5-16-85.
b Ratings taken 5-21-85: Scale 0 to 5, 0 - no burn to 5 - maximum burn.
c Ratings taken 5-21-85: Scale 0 to 5, 0 - pale, chlorotic condition to 5 - deep green color.

EXAMPLE III

Methyl triazone (36% N) and hydroxyethyl triazone (29%N) were evaluated for phytotoxicity, color and growth on a bluegrass sod farm near Allentown, N.J. at nitrogen rates of 1.5, 3.0 and 6.0 pounds of nitrogen per 1000 sq. ft.. The control at this location was a 20%N urea solution applied at the same nitrogen rates in a spray solution of 4.0 gal./1000 sq. ft.

As noted in Table III, less phytotoxicity occurred for the triazone products at all nitrogen rates.

TABLE III

| N. Source (N. a) | Rate | Phytotox. (Note b) | Color (Note c) | Growth (Note d) |
| --- | --- | --- | --- | --- |
| Methyl triazone | 1.5 | 1.0 | 4 | 2 |
| Hydroxyethyl triazone | 1.5 | 1.0 | 4 | 2 |
| Urea | 1.5 | 2.0 | 4 | 2 |
| Methyl triazone | 3.0 | 2.0 | 4 | 3 |
| Hydroxyethyl triazone | 3.0 | 2.0 | 5 | 4 |
| Urea | 3.0 | 3.0 | 5 | 4 |
| Methyl triazone | 6.0 | 3.0 | 4 | 3 |
| Hydroxyethyl triazone | 6.0 | 3.0 | 4 | 3 |
| Urea | 6.0 | 4.0 | 5 | 5 |

Notes:
a Treatments applied 8-1-85.
b Ratings taken 8-6-85: Scale 0 to 5; 0 - no burn to 5 - maximum burn.
c Ratings taken 8-15-85: Scale 0 to 5; 0 - pale, chlorotic condition to 5 - deep green color.
d Ratings taken 8-15-85: Scale 0 to 5; 0 - no growth compared to untreated to 5 - maximum growth.

EXAMPLE IV

Two solid triazone products; methyl triazone (36%N) (water-insoluble triazone) and hydroxyethyl triazone (29%) (water-insoluble triazone) were sent from our Geismar, La., Development Laboratory (GDL) to researchers at University of Georgia, Experiment, Georgia for field evaluation as a fertilizer nitrogen source for a turf grass, tall fescue. These products were compared with conventional solid nitrogen sources, urea and ammonium nitrate. The field study was initiated on Nov. 6, 1985; whereby, each of the above products and a control (untreated) were applied at nitrogen rates of 1.0 and 3.0 pounds per 1000 sq. ft.. Commercial nitrogen applications are generally applied at 1.0 lbs. N/1000 sq. ft..

Experiments of this type below conducted at the University of Georgia are designed to measure such factors as phytotoxicity (leaf burning), color of the grass, quality of the turf, growth (clippings), nitrogen content of the leaf tissue, and soil pH changes. The test results are shown in the following Table IV.

The following Table IV illustrates an evaluation of N sources on turf (fall fescue) applied at 1.0 lb. N/1000 sq. ft.

TABLE IV

| Product (N. a) | Phytotox. 11-8-85 (N. b) | Color Rating (N. c) | Quality Rating 12-5-95 (N. d) | Clippings (grams) 12-17-85 | Total Leaf N (%) 12-17-85 |
| --- | --- | --- | --- | --- | --- |
| Methyl triazone | 9.0 | 7.7 | 7.3 | 38 | 3.12 |
| Hydroxyethyl triazone | 8.3 | 8.0 | 7.5 | 50 | 3.17 |
| Urea | 8.7 | 7.5 | 6.5 | 41 | 3.13 |
| Ammonium Nitrate | 6.3 | 7.7 | 7.0 | 35 | 3.20 |
| Control | 9.0 | 5.8 | 5.3 | 45 | 2.61 |

Notes:
a Applied on 11-6-85.
b Ratings 1 to 9 where 1 = all leaves burned and 9 = no burn.
c Color rating 1 to 9 where 1 = all brown and 9 = dark green.
d Quality rating 1 to 9 where 1 = no live turf and 9 = ideal.

EXAMPLE V

The following Table V is further study identical to that of Table V, except here applying the fertilizer at a rate of 3.0 lbs. N/1000 sq. ft.

TABLE V

| Product (N. a) | Phytotox. (n. b) 11-8-85 | Color Rating (N. c) 12-9-85 | Quality Rating (N. d) 12-9-85 |
| --- | --- | --- | --- |
| Methyl triazone | 9.0 | 8.0 | 6.7 |
| Hydroxyethyl triazone | 8.0 | 7.8 | 7.3 |
| Urea | 6.3 | 7.7 | 7.3 |
| Ammonium nitrate | 4.0 | 7.2 | 6.7 |
| Control | 9.0 | 5.8 | 5.3 |

Notes:
a Applied on 11-6-85.
b Phytotoxicity rating 1 to 9 where 1 = all leaves burned and 9 = no burn.
c Color rating 1 to 9 where 1 = all brown and 9 = dark green.
d Quality rating 1 to 9 where 1 = no live turf and 9 = ideal.

Data from the two preceding tables indicate that methyl triazone and hydroxyethyl triazone are safer nitrogen sources than urea and ammonium nitrate. When applied at 3.0 lbs. N/1000 sq. ft., no injury was observed from methyl triazone and minimum injury from hydroxyethyl triazone (Table V). Sever phytotoxicity was noted for ammonium nitrate and urea.

Turf color and quality ratings for the triazones were as good or better than for ammonium nitrate and urea.

EXAMPLE VI

A further evaluation was conducted at Kansas State University, evaluating nitrogen sources for mineralization and volatilization characteristics, as shall be illustrated in the following Tables VI, VII, VIII, and IX. The researchers evaluated methyl triazone and hydroxyethyl triazone for nitrogen release characteristics as measured by the mineralization rate and formation of nitrate nitrogen. The nitrogen volatilization potential was also evaluated. Urea and IBDU were included as standard nitrogen products for comparison. Urea is recognized as a nitrogen source that mineralizes and volatiles rather quickly, while IBDU is considered to be one of the slowest to mineralize.

Release experiments were established, whereby the nitrogen sources were mixed with soil at 100 ugN/g of soil and incubated for 50 days at 12 degrees Centigrade and for 24 days at 22 and 32 degrees Centigrade. Soil samples were taken at 4, 14, 24, 36 and 50 days for the lowest temperature and at 2, 4, 8 and 24 days for the two highest temperatures. These samples were analyzed for nitrate nitrogen. Results are expressed as % of nitrogen applied and shown in the following above-noted Tables VI, VII and VIII.

The volatilization experiment was established whereby the four solid products were applied on the soil surface at 296 ugN/g soil (equivalent to 105 kg. N/ha and incubated at 22 degrees Centigrade. Results are shown in Table IX.

As illustrated, nitrogen was released from the triazone based products at a much slower rate than urea. This release pattern is desirable because a more uniform and consistent supply of nitrate nitrogen would be available for plant growth. A rapid release of nitrogen from urea can lead to a loss of fertilizer nitrogen from (1) volatilization losses into the atmosphere, (2) leaching losses from the nitrate ion moving through the soil profile and into the ground water and (3) denitrification losses which is the biochemical reduction of nitrate nitrogen under anaerobic conditions.

The release pattern was not expected to be as slow as IBDU (isobutylidenediurea).

Volatilization losses from surface applied urea can be over 50% (Volk, G. M. Volatile Loss of Ammonia Following Surface Application of Urea to Turf or Bare Soil, Agron. J. 51: 746–749. 1959.) and represents a major problem for this commonly used nitrogen source. As illustrated in Table IX the triazone products loss less than 1% of applied nitrogen; whereas, urea lost 17%.

In the following Table VI, for the several different fertilizers above-noted, the release and mineralization is expressed in percentages ranging from zero to 100 percent, and for differing periods of elapsed time, namely at 4 days and 14 days and 24 days and 36 days and at 50 days, for each of urea, IBDU, methyl triazone, and hydroxyethyl triazone.

TABLE VI

Release and Mineralization of Nitrate Nitrogen from Organic Sources at 12 degrees Centigrade.

| | Expressed in % | | | | |
|---|---|---|---|---|---|
| No. of days: | 4 | 14 | 24 | 36 | 50 |
| Urea | 15 | 57 | 82 | 83 | 85 |
| IBDU | 2 | 4.5 | 4 | 7 | 16 |
| Methyl Triaz. | 4 | 6 | 8.5 | 10.5 | 12 |
| Hydroxyethyl Triazone | 2 | 2.5 | 2.9 | 3.7 | 4.5 |

TABLE VII

Release and Mineralization of Nitrate Nitrogen from Organic Sources at 22 degrees Centigrade.

| | Expressed in % | | | |
|---|---|---|---|---|
| No. of days: | 2 | 4 | 8 | 24 |
| Urea | 16.5 | 38 | 84 | 88 |
| IBDU | 4 | 5.4 | 8 | 18.5 |
| Methyl Triaz. | 5 | 7.5 | 9 | 20 |
| Hydroxyethyl Triazone | 2 | 3 | 3 | 6.5 |

Release and Mineralization of Nitrate Nitrogen from Organic Sources at 32 degrees Centigrade.

| | Expressed in % | | | |
|---|---|---|---|---|
| No. of days: | 2 | 4 | 8 | 24 |
| Urea | 29.8 | 63.6 | 84.6 | 81 |
| IBDU | 12 | 17 | 25 | 29 |
| Methyl Triaz. | 9 | 14.4 | 24 | 47 |
| Hydroxyethyl Triazone | 5 | 6 | 10 | 19 |

TABLE IX

Release and Volatilized Nitrogen from Organic Sources at 22 degrees Centigrade.

| | Expressed in % | | | |
|---|---|---|---|---|
| No. of days: | 4 | 8 | 14 | 24 |
| Urea | 12 | 16.5 | 15.5 | 16.8 |
| IBDU | 0 | .1 | .1 | .1 |
| Methyl Triaz. | .4 | .6 | .8 | .9 |
| Hydroxyethyl Triazone | 0.1 | .1 | .3 | .3 |

EXAMPLE VII

This example is directed to one of many experiments, in which water-insoluble triazone was produced, in this experiment the produced product being methyl triazone.

| Formulation | Wt. % |
|---|---|
| UF-85 (BORDEN) | 31.2 |
| (26.8% urea, 57.7% formaldehyde) | |
| Urea | 49.2 |
| 25% KOH solution | 3.6 |
| Methylamine (40% solution) | 16.0 |

Procedure:

A. Mix together the UF-85 and urea.

B. Slowly added the methylamine solution.

C. Heat to 90 degrees Centigrade (plus or minus 0.5 degrees Centigrade for one hour and adjust pH at about 9.0 (plus or minus about 0.3) for one hour by slow and gradual addition of KOH solution.

E. Maintain temp. at about 90 degrees Centigrade (plus or minus about 0.5 degrees Centigrade) for an additional hour.

F. Cool and package.

| Break-down: | TIME | TEMP (Centig.) | pH |
|---|---|---|---|
| UF-85/Urea | 8:46 | 17.6 | 4.5 |
| Add methylamine | 9:00 | 47 | 9.4 |
| Turn steam on | 9:00 | 88 | 8.8 |
| Start KOH addition | 9:20 | 88 | 8.8 |
| END KOH addition | 10:20 | 90 | 9.2 |
| END cook | 11:20 | 90 | 9.1 |
| END batch | 12:35 | 16 | 11.1 |

Heavy crystallization on standing 24 hours. Filtered off the crystals, and washed with reagent alcohol. Again filtered off crystals and dried at 50 degrees Centigrade in vacuum oven.

EXAMPLE VIII

This example is typical of what proved to be the best known method eventually developed for the production of insoluble triazones from either urea (or substituted form(s) thereof or thiourea (or substituted form(s) thereof,) even though this particular method has been found to be best for the non-thiotriazone production.

The laboratory procedure that has been followed has been as follows, recited in terms of steps.

(1) Mix together the urea (or substituted urea), the urea-formaldehyde mixture (commercially known as typicall UF-85), and water (and/or other diluent).

(2) Adjust pH to 9.0 with 45% KOH aqueous solution (a typical standard laboratory dilution).

(3) Slowly add the amine (and/or ammonia) while cooling to the extent required to keep the temperature below the boiling point of the amin. (The boiling point of the amines vary from about 45 degrees to over 100 degrees Centigrade, depending upon which amine is utilized. One must not allow the temperature to get above about 85 degrees Centigrade in any case during the amine addition.)

(4) Heat to 90 degrees Centigrade and maintain temperature at 90 degrees (plus or minus about 1 degree) Centigrade for about 20 minutes while holding pH at about 9.0 (plus or minus about 0.3) by the slow addition of 45 percent KOH solution.

(5) End pH control but continue temperature control at 90 degrees Centigrade (plus or minus about one degree) Centigrade for an additional about ten minutes.

(6) Cool to room temperature.

(7) Transfer the reaction mix to a 4 liter beaker and cool for about 48 to 72 hours at 1 degree Centigrade (34 degrees Fahrenheit). In some of the products, crystallization occurs during the amine addition and cooling lower than room temperature is not required.

(8) Filter off the crystals and wash with reagent alcohol twice, or with water. Crystals may be removed from the mother liquor by filtration, centrifuging, or sedimentation or any other desired method that would not be detrimental to the crystals.

(9) Oven dry the crystals at about 70 degrees Centigrade for 48 hours. Products may be spray dried, freeze dried or oven dried or dried by any other desired applicable method that does not damage the crystals.

Products produced by this last-described method are as follow:

| Amine used (below) | Name of resulting insoluble triazone |
|---|---|
| Ethanol amine | 5-B, hydroxyethyl triazone |
| Methylamine | 5-methyl triazone |
| Ethylamine | 5-ethyl triazone |
| Ethylene diamine | ethylene ditriazone |
| Diamino propane | isopropyl ditriazone |
| 1,3 diamino, 2 hydroxy propane | 1, 3 ditriazone, 2 hydroxypropane |
| Tris (2 amino ethyl) amine | Tris (ethyl triazone) amine |
| 1-adamantan amine | S—adamatane triazone |
| Adenine | 5 purine triazone |
| Allantoin | 1, triazone, 3, (2,5 dioxo-4-imidazolidinyl urea 3-amino-5,6-dimethyl-1,2,4-triazine 5-(5,6-dimethyl-1,2-4-triazone) triazon |
| 6-amino-1,3-dimethyl uracil | 5-(1,3 dimethyl uracil) triazone |
| Furfurylyamine | 5(furfuryl) triazone |

EXAMPLE IX

This Example follows a typical procedure of the other thus-far optimal method researched and developed, for producing insoluble triazone, but found best suited for, i.e. best results in, production of the thiortriazones, according to the following typical procedure followed in the laboratory.

(1) Mix together the urea (or substituted urea), the urea-formaldehyde mixture (i.e. typically a mixture of commercially available mixture of urea and formadelhyde known as UF-85), and water (and/or other diluent).

(2) Slowly add the amine (and/or ammonia) while cooling sufficiently as might be required to keep the temperature below the boiling point of the amine. The boiling point of the amines varies for different amines from about 45 degrees Centigrade to about (or more than) 100 degrees Centigrade. Do not allow the temperature to get above about 85 degrees Centigrade in situations utilizing the amine addition.

(3) Allow mixing to continue for at-least about 30 minutes. Preferably mix for at-least about 15 minutes up to about 3 hours.

(4) Cool to about room temperature.

(5) Transfer the reaction mix to a 4 liter beaker and cool for about 48 to about 72 hours at about 1 degree Centigrade (34 degrees Fahrenheit). In some of the products, crystallization occurs during the amine addition and cooling lower than room temperature is not required.

(6) FIlter off the crystals and wash with reagent alcohol (or water) twice. Crystals may be removed from the mother liquor by filtration, centrifuging, sedimentation or any desired method.

(7) Oven dry the crystals at about 70 degrees Centigrade for about 48 hours. Product may be spray dried, freeze dried or oven dried, or dried by any other desired applicable method that does not damage the cystals.

Typical insoluble thiotriazones optimally produced by the last-described above method of Example IX include the following:

| REACTANTS | THIOTRIAZONE CPD. |
|---|---|
| (1) Formaldehyde; thiourea; ammonia | (unsubstituted) Thiotriazone. |
| (2) Formaldehyde; thiourea; methyl amine | 5-B—ethanol thiotriazone |
| (3) Formaldehyde; thiourea; ethylamine | 5-ethyl thiotriazone |
| (4) Formaldehyde; thiourea; ethylene diamine | 5, 5'-ethylene dithiotriazone |
| (5) Acetaldehyde; thiourea; ethanolamine | 4,6-dimethyl, 5 B—hydroxyethyl thiotriazone. |

It is within the scope of this invention to make variations and substitution of equivalents obvious to a person of ordinary skill in this art.

We claim:

1. A water-insoluble thiotriazone of the structural formula:

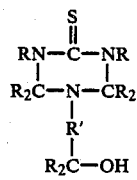

in which R is hydrogen, alkyl, and/or alkyl-substituted alkyl, and in which R' is alkyl-substituted alkylene, or alkylene.

2. A water-insoluble thiotriazone of the structure formula:

$$\begin{array}{c} \text{S} \\ \parallel \\ \text{RN}-\text{C}-\text{NR} \\ | \qquad | \\ \text{R}_2\text{C}-\text{N}-\text{CR}_2 \\ | \\ \text{R}_2\text{C}-\text{OH} \end{array}$$

where R is hydrogen, alkyl, and/or alkyl-substituted alkyl.

3. A water-insoluble thiotriazone of the structural formula:

$$\begin{array}{c} \text{S} \\ \parallel \\ \text{RN}-\text{C}-\text{NR} \\ | \qquad | \\ \text{R}_2\text{C}-\text{N}-\text{CR}_2 \\ | \\ \text{R}' \end{array}$$

in which R is hydrogen, alkyl or alkyl-substituted-alkyl, and where R' is alkyl or alkyl-substituted alkyl, or where R' is alkyl or alkyl-substituted alkyl, cycloalkyl, or hydroxyalkyl.

4. A water-insoluble thiotriazone entitled 5-methyl thiotriazone of the structural formula:

$$\begin{array}{c} \text{S} \\ \parallel \\ \text{HN}-\text{C}-\text{NH} \\ | \qquad | \\ \text{H}_2\text{C}-\text{N}-\text{CH}_2 \\ | \\ \text{CH}_3 \end{array}$$

5. A water-insoluble thiotriazone entitled 5-B-ethanol thiotriazone having the structural formula:

$$\begin{array}{c} \text{S} \\ \parallel \\ \text{HN}-\text{C}-\text{NH} \\ | \qquad | \\ \text{H}_2\text{C}-\text{N}-\text{CH}_2 \\ | \\ \text{C}_2\text{H}_4\text{OH} \end{array}$$

6. A water-insoluble thiotriazone entitled 4,6 dimethtyl-5-B-ethanol thiotriazone having the structural formula:

$$\begin{array}{c} \text{S} \\ \parallel \\ \text{HN}-\text{C}-\text{NH} \\ | \qquad | \\ \text{CH}_3-\text{C}-\text{N}-\text{CH}-\text{CH}_3 \\ \text{H} \quad | \\ \quad \text{C}_2\text{H}_4\text{OH} \end{array}$$

7. A water-insoluble thiotriazone entitled 1-3 dimethyl thiotriazone.

8. A water-insoluble thiotriazone entitled 1-3 dimethyl-5-Beta ethanol thiotriazone.

9. A water-insoluble thiotriazone entitled 4-6 dimethyl thiotriazone.

10. A water-insoluble thiotriazone entitled 1,3,4,6 tetramethyl thiotriazone.

11. A water-insoluble thiotriazone entitled, 5,5' ethylene dithiotriazone of the structural formula:

$$\begin{array}{c} \text{S} \\ \parallel \\ \text{HN}-\text{C}-\text{NH} \\ | \qquad | \\ \text{H}_2\text{C}-\text{N}-\text{CH}_2 \\ | \\ \text{H}_2\text{C}-\text{CH}_2 \\ | \\ \text{H}_2\text{C}-\text{N}-\text{CH}_2 \\ | \qquad | \\ \text{HN}-\text{C}-\text{NH} \\ \parallel \\ \text{S} \end{array}$$

12. A water-insoluble dithiotriazone of the structural formula:

$$\begin{array}{c} \text{S} \\ \parallel \\ \text{RN}-\text{C}-\text{NR} \\ | \qquad | \\ \text{R}_2\text{C}-\text{N}-\text{CR}_2 \\ | \\ \text{R}_2\text{C}-\text{CR}_2 \\ | \\ \text{R}_2\text{C}-\text{N}-\text{CR}_2 \\ | \qquad | \\ \text{RN}-\text{C}-\text{NR} \\ \parallel \\ \text{S} \end{array}$$

in which R is hydrogen, alkyl, and/or alkyl-substituted alkyl.

13. A water-insoluble thiotriazone entitled 1-3-5-trimethyl thiotriazone.

14. A water-insoluble thiotriazone entitled 4,6,5, trimethyl thiotriazone.

15. A water-insoluble thiotriazone entitled 4-6 diethyl thiotriazone.

16. A water-insoluble thiotriazone entitled 4-6 diethyl-5-B hydroxyethyl thiotriazone.

17. A water-insoluble thiotriazone entitled ethyl thiotriazone.

18. A water-insoluble triazone entitled S-adamantane triazone.

19. A water-insoluble triazone entitled 5-(5,6-dimethyl-1-2-4-triazine)triazone.

20. A water-insoluble triazone entitled 5-(1,3 dimethyl uracil)triazone.

21. A water-insoluble triazone entitled 5(furfuryl)triazone.

22. A water-insoluble triazone entitled 5-hydantoinamide, triazone.

23. A water-insoluble triazone entitled 5 purine triazone.

24. A water-insoluble triazone entitled 4,6-propyl-5-betahydroxyethyl triazone.

25. A water-insoluble triazone entitled 5-methyl triazone.

26. A water-insoluble triazone entitled ethyl triazone.

27. A water-insoluble ditriazone entitled isopropyl ditriazone.

28. A water-insoluble ditriazone entitled ethylene ditriazone.

29. A water-insoluble triazone entitled 5-B-hydroxyethyltriazone.

30. A water-insoluble triazone entitled 5,5'-ethylene ditriazone.

31. A water-insoluble triazone entitled 1, 3 ditriazone, 2 hydroxypropane.

32. A water-insoluble triazone entitled tris(ethyl triazone)amine.

33. A water-insoluble triazone entitled 1, triazone, 3, (2, 5 dioxo-4-imidazolininyl)urea.

34. A water-insoluble triazone entitled 5-methyl thiotriazone.

35. A water-insoluble triazone entitled ethyl thiotriazone.

36. A water-insoluble triazone entitled ethanol thiotriazone.

37. A method of fertilizing vegetation comprising applying to said vegetation an effective amount of an insoluble triazone according to any one of claims 1 through 28.

38. A method of fertilizing sod comprising applying to said sod an effective amount of an insoluble triazone according to any one of claims 1 through 28.

39. A method of fertilizing foliage comprising spraying onto said foliage an aqueous mixture comprising an effective amount of an insoluble triazone according to any one of claims 1 through 28.

40. A method of making a water-insoluble triazone of any one of claims 1 through 36, comprising employing initial reactants comprising mixing together a urea-type compound-source and an aldehyde-type compound-source and a diluent in a diluting amount sufficient for the urea-type compound-source and the aldehyde-type compound-source to be admixed therein sufficiently to form a reaction mixture; to said reaction mixture, first-adding caustic in an amount sufficient to adjust pH to a pH with a pH range of from about pH 8.6 to about pH 9.3, and sufficiently to form a pH-adjusted reaction mixture; thereafter to said pH-adjusted reaction mixture, adding an ammonia-type compound-source sufficiently to form an ammonia or amine-type reaction product, when said ammonia-type compound-source includes an amine, rate of addition of said ammonia-type compound-source being sufficiently slow during said adding as to maintain temperature up to a temperature below a boiling point of said amine, relative to rate of cooling of the ammonia or amine-type reaction product; thereafter heating said amine-type reaction product at a temperature within a temperature ranging from about 85 degrees Centigrade to about 93 degrees Centigrade for an initial heating period ranging from about 15 minutes up to abiout 30 minutes sufficiently to form a final reaction product mixture while second-adding caustic which is predominantly potassium hydroxide in an amount sufficiently to substantially maintain pH within said pH range during said initial heating period; thereafter terminating further addition of caustic, while thereafter continuing heating said final reaction product mixture within said temperature range for an additional period ranging from about 5 minutes to about 25 minutes, sufficiently to form a cooked product mixture; thereafter cooling said cooked product mixture sufficiently that insoluble triazone becomes substantially crystallized triazone apart from remaining liquid product and substances dissolved therein; and thereafter separating said crystallized triazone from said remaining liquid product and substances dissolved therein.

41. The method of claim 40, in which said diluent includes a major proportion of water, and in which said temperatures of said temperature range is maintained within a second temperature range of from about 89 to about 91 degrees Centigrade, in which said first-adding and said second-adding of caustic is in an amount such that pH-alkalinities of said pH range is maintained between about pH8.9 and pH 9.1, heating during said initial heating ranging from about 15 to about 25 minutes, and said additional heating ranging from about 7 minutes to about 15 minutes, and in which said cooling comprising cooling-down said cooked-product mixture to at-least below about 30 degrees Centigrade.

42. The method of claim 41, in which said urea-type compound source is at-least predominantly urea, and in which said aldehyde-type compound source comprises at-least predominantly formaldehyde.

43. The method of claim 42, in which said cooling, prior to said separating, comprises cooling said cooked product for a final cooling-period of at-least 48 hours at a temperature of between about 0.2 degrees and 6 degrees Centigrade.

44. The method of claim 43, including, after said separating, drying said crystallized triazone at a temperature of from about 60 degrees to about 75 degrees Centigrade for at-least about 36 hours.

45. The method of claim 42, in which said cooling, prior to said separating, comprises cooling said cooked product for a final cooling period of at-least about 60 hours at a temperature of between about 0.5 degrees and about 2 degrees Centigrade, and after said separating, drying said crystallized triazone at a temperature of from about 65 degrees to about 72 degrees Centigrade for at-least about 44 hours.

46. A method of making a water-insoluble triazone of any one of claims 1 through 36, comprising employing initial reactants comprising mixing together a urea-type compound-source and an aldehyde-type compound-source and a diluent in a diluting amount sufficient for the urea-type compound source and the aldehyde-type compound-source to be admixed therein sufficiently to form a reaction mixture; to said reaction mixture, thereafter adding an ammonia-type compound-source sufficiently to form an ammonia or amine-type reaction product sufficiently to form an ammonia or amine-type product, and when said ammonia-type compound-source includes an amine, rate of addition of said ammonia-type compound-source being sufficiently slow during said adding as to maintain temperature up to a temperature below a boiling point of said amine, relative to rate of cooling of said ammonia or amine-type compound-source; thereafter cooling said ammonia or amine-type produce sufficiently that insoluble triazone becomes substantially crystallized as crystallized triazone apart from remaining liquid product and substances dissolved therein; and thereafter separating said crystallized triazone from said remaining liquid product and substances dissolved therein.

47. The method of claim 46, in which said mixing is continued for a period of at-least about 15 minutes, in which said diluent includes a major proportion of water, and in which said cooling comprises cooling-down said ammonia or amine-type product to at-least below about 30 degrees Centigrade.

48. The method of claim 47, in which said urea-type compound comprises at-least predominantly a thiourea, and in which said aldehyde-type compound comprises at-least predominantly formaldehyde.

49. The method of claim 48, in which said cooling, prior to said separating, comprises cooling said ammonia or amine-type product for a final cooling-period of at-least 48 hours at a temperature between about 0.2 degrees and 6 degrees Centigrade.

50. The method of claim 49, including, after said separating, drying said crystallized triazone at a temperature of from about 60 degrees to about 75 degrees Centigrade for at-least about 36 hours.

51. The method of claim 49, in which said cooling, prior to said separating comprises cooling said cooked product for a final cooling period of at-least about 60 hours at a temperature of between about 0.5 degrees and about 2 degrees Centigrade, and after said separating, drying said crystallized triazone at a temperature of from about 65 degrees to about 72 degrees Centigrade for at-least about 44 hours.

* * * * *